United States Patent [19]
Ryan

[11] Patent Number: 5,137,514
[45] Date of Patent: Aug. 11, 1992

[54] INFLATION SYRINGE ASSEMBLY FOR PERCUTANEOUS TRANSLUMINAL ANGIOPLASTY

[75] Inventor: James P. Ryan, Amherst, N.H.

[73] Assignee: Accumed Systems, Inc., Southfield, Mich.

[21] Appl. No.: 607,917

[22] Filed: Nov. 1, 1990

[51] Int. Cl.⁵ ............................................. A61M 29/00
[52] U.S. Cl. ...................................... 604/99; 604/211; 604/224
[58] Field of Search .................... 604/97–100, 604/121, 208, 209, 211, 224, 227

[56] References Cited

U.S. PATENT DOCUMENTS

| | | | |
|---|---|---|---|
| 2,475,939 | 7/1949 | Applezweig | 128/218 |
| 2,745,575 | 5/1956 | Spencer | 222/327 |
| 3,020,663 | 2/1962 | Newson | 42/70 |
| 3,905,365 | 9/1975 | Colombo | 128/218 |
| 4,275,729 | 6/1981 | Silver et al. | 128/218 |
| 4,312,343 | 1/1982 | LeVeen et al. | 128/218 |
| 4,322,022 | 3/1982 | Bergman | 222/327 |
| 4,332,254 | 6/1982 | Lundquist | 128/344 |
| 4,370,982 | 2/1983 | Reilly | 604/98 |
| 4,429,724 | 2/1984 | Dorros et al. | 141/27 |
| 4,439,185 | 3/1984 | Lundquist | 604/97 |
| 4,583,974 | 4/1986 | Kokernak | 604/211 |
| 4,654,027 | 3/1987 | Dragan et al. | 604/99 |
| 4,655,749 | 4/1987 | Fischione | 604/98 |
| 4,723,938 | 2/1988 | Goodin et al. | 604/99 |
| 4,743,230 | 5/1988 | Nordquest | 604/97 |
| 4,832,692 | 5/1989 | Box et al. | 604/99 |
| 4,838,864 | 6/1989 | Peterson | 604/100 |
| 4,929,238 | 5/1990 | Baum | 604/208 |
| 4,940,459 | 7/1990 | Noce | 604/98 |
| 5,019,041 | 5/1991 | Robinson et al. | 604/211 |
| 5,047,015 | 10/1991 | Foote et al. | 604/224 |

FOREIGN PATENT DOCUMENTS 0228162 10/1986 European Pat. Off. .

OTHER PUBLICATIONS

Product literature, "The Wizard", USCI Division, C. R. Bard, Inc.
Product literature, "ACS Accessories", ACS, a subsidiary of Eli Lilly and Company.
Product literature, "Inflation Pro", American Edwards Laboratories.

*Primary Examiner*—John D. Yasko
*Assistant Examiner*—Anthony Gutowski
*Attorney, Agent, or Firm*—Hayes, Soloway, Hennessey & Hage

[57] ABSTRACT

An angioplasty syringe has a half-threaded surface which engages a threaded hydraulic plunger for generating balloon inflating pressure. The threaded nut is part of a component having a cam which engages a cam is part of a pistol trigger. The cam positively raises and closes the threaded surface depending upon the trigger position.

16 Claims, 2 Drawing Sheets

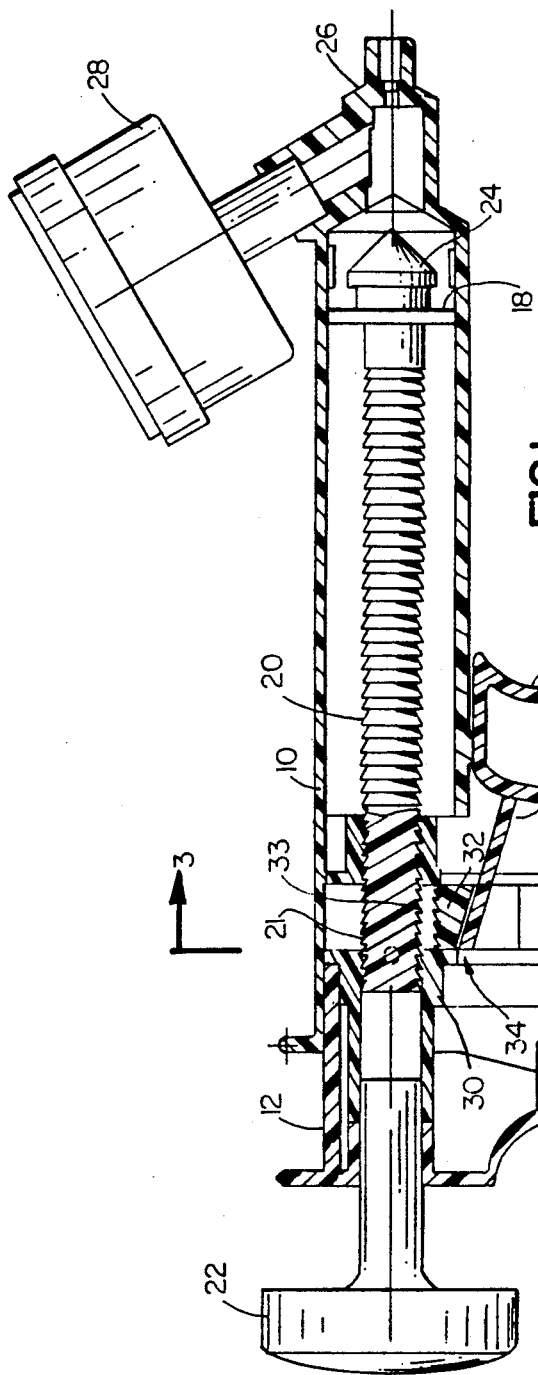
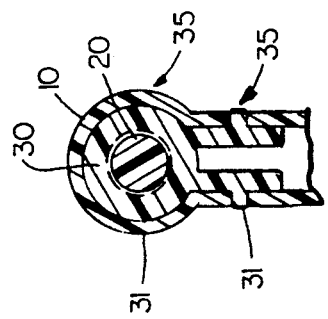
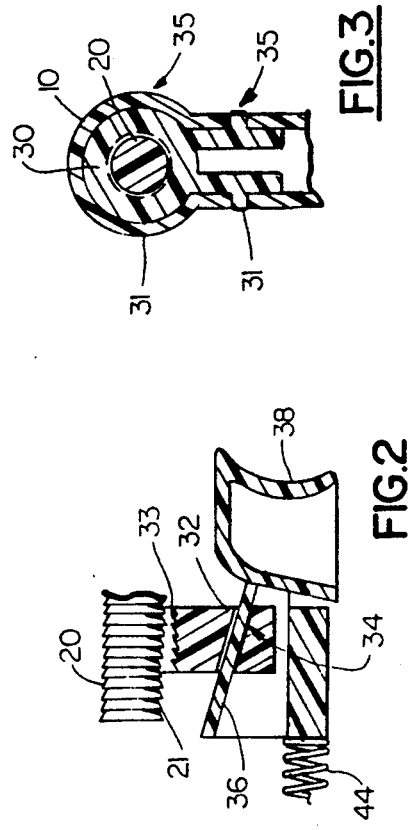

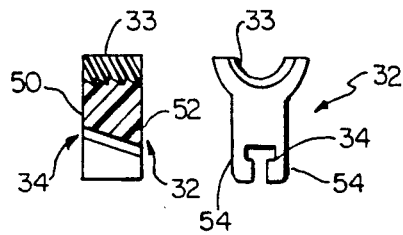
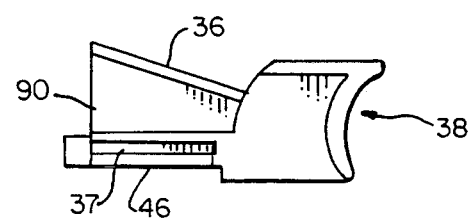
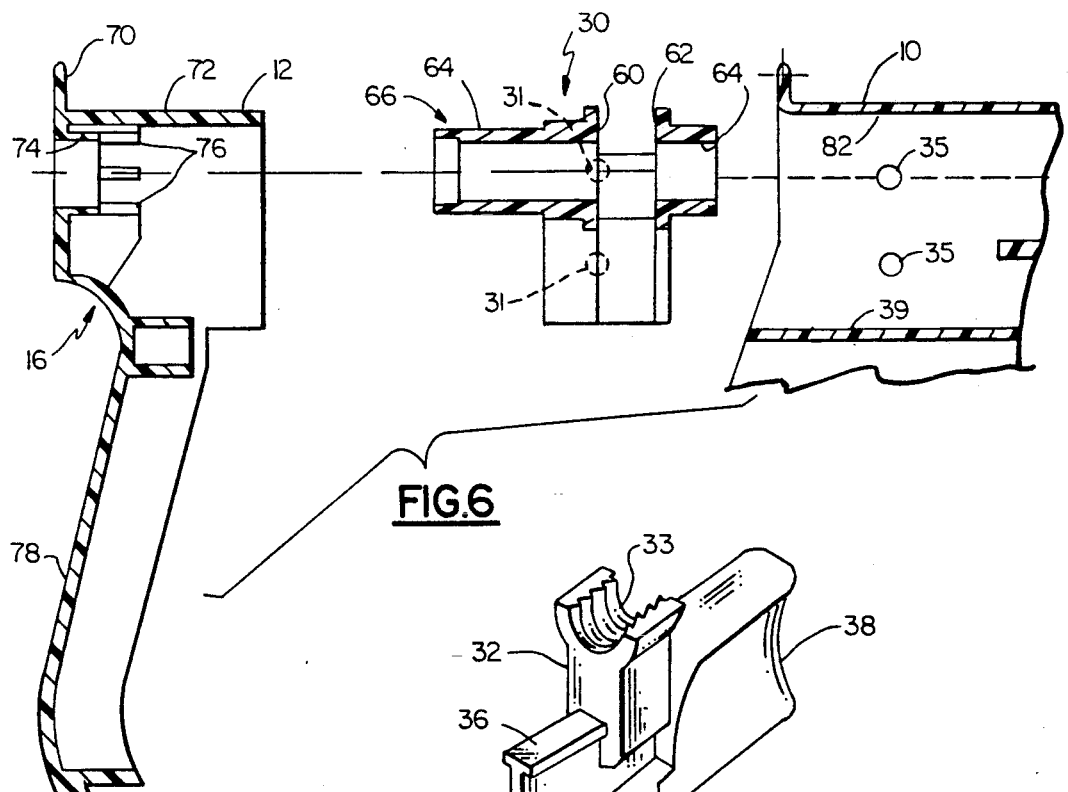
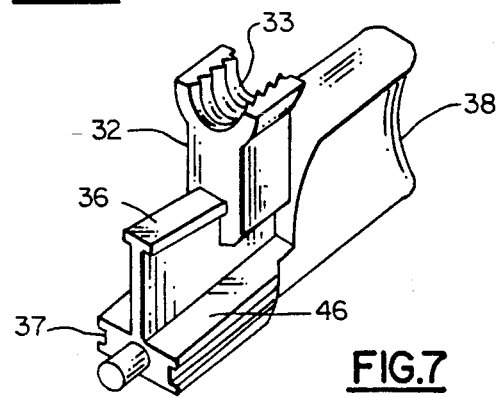

INFLATION SYRINGE ASSEMBLY FOR PERCUTANEOUS TRANSLUMINAL ANGIOPLASTY

BACKGROUND OF THE INVENTION

The present invention is directed to an inflation device, in the form of a syringe assembly, for pressurization and depressurization of a balloon catheter.

The General type of pressurization device is typified by prior U.S. Pat. No. 4,832,692, May 23, 1989 to Box et al. In such a device, a moveable piston is provided for initial pressurization of the fluid in communication with the balloon catheter. The final pressurization is achieved by threaded engagement between a half nut and a rod supporting the piston so that rotation of the rod will advance the piston and the piston will gradually increase the pressure in a precisely controlled amount. To release the pressure, the half nut is moved radially away from the threaded rod.

The present invention is directed to an improved system for controlling the positioning and release of the half nut which operates in conjunction with the threaded piston. A principal objective is to provide a very simple system which can be operated by one hand, which can't be inadvertently released and which is very simple to manipulate both for pressurization and release. This system is inexpensive and provides positive motion of the threaded component in both the engagement and release directions. Other patents of general background interest to the present invention are the following:

| 4,583,974 | Kokernak | April 22, 1986 |
| 4,654,027 | Dragan et al. | March 31, 1987 |
| 2,475,939 | Applezweig | July 12, 1949 |
| 4,919,121 | Rydell | April 24, 1990 |

BRIEF DESCRIPTION OF THE INVENTION

The present invention is particularly directed to a system for engaging and disengaging a half-threaded surface from the piston which controls the pressurization of the angioplasty balloon catheter. In the preferred form of the invention, the threaded surface is part of a component which is arranged to be moved upwardly and downwardly inside of a pistol grip which extends downwardly from a cylinder in which the piston moves. Thus the cylinder constitutes the barrel of the pistol and the pistol grip carries a trigger which preferrably moves in a direction parallel to the axis of the cylinder. This trigger has a cam surface which engages a cam surface carried by the component. The trigger cam surface positively engages the component cam surface to move the component away from the threaded surface when the trigger is moved towards the handle and moves the component toward the threaded surface when the trigger is moved in a second direction parallel to the axis of the barrel and away from the pistol handle. A spring means is provided for urging the trigger in said second direction.

BRIEF DESCRIPTION OF THE DRAWINGS

In order to more fully understand the invention, reference should be made to the following detailed description taken in connection with the accompanying drawings wherein like numerals depict like parts, and wherein:

FIG. 1 is a side view, in cross-section, of an inflation syringe assembly according to the present invention;

FIG. 2 is a side view showing details of parts of the trigger mechanism according to the present invention;

FIG. 3 is a partial sectional view taken along the line 3—3 of FIG. 1;

FIGS. 4A and 4B are sectional and end views respectively, showing additional details of parts of the trigger mechanism according to the present invention;

FIG. 5 is a side view showing additional details of parts of the trigger mechanism according to the present invention;

FIG. 6 is an exploded view showing the relationship of the various parts of the syringe assembly of the present invention; and FIG. 7 is an isometric view of the assembled trigger and assembly of the present invention.

DETAILED DESCRIPTION OF THE INVENTION

Reference should now be had to FIGS. 1 and 2 which are diagramatic and schematic partially sectional views of a preferred form of the present invention, particularly as adopted to a system of the type generally shown in the previously mentioned U.S. Pat. No. 4,832,692.

Referring now to FIGS. 1 and 2, the preferred form of the invention includes a plastic cylinder (10) which is completed by a rear plastic section (12) from which a hollow pistol grip (14) depends. In the preferred form of the invention, hollow rear section (12) is formed with a hollow plastic casting (16) which can be permanently secured to the rear section of the cylinder (10). Portions (14) and (16) form the pistol grip. A piston (18), of normal type used in angioplasty pumps, is mounted in the cylinder (10) on a threaded rod (20) which controls the axial movement of the piston (18). A handle (22) on the rear of the rod (20) provides axial movement of the rod as well as rotary movement of the rod. Threads (21) are provided on the exterior surface of the rod (20). A usual rubber tip (24) is provided to form the end of the piston (18).

A bearing member (30) supports the rod (20) coaxially in the cylinder (10). Mounted in the bearing member (30) is a half threaded component (32) having screw threads (33) which are arranged to engage the corresponding screw threads (21) on the rod (20) when the component (32) is in the upward position as shown on FIG. 1. When the component (32) is in the lower position, as shown in FIG. 2, the rod (20) is free for motion axially along the cylinder (10). An angled slot (34) in the component (32) constitutes a cam surface which engages a cam surface (36) carried by a trigger (38). This trigger (38) is normally urged to the right, as shown in FIG. 1, by spring (40) held in a bushing (42) and supported on a rod (44) which is integrally formed in a portion (46) of the trigger (38). This portion (46) preferably contains a slot (37) which engages a rib (39) on the interior of the hollow plastic grip (14). (See FIG. 6.)

With this arrangement, when there is no pressure on the trigger (38), the threaded component (32) is pushed upwardly into engagement with the threads (21) on the rod (20). For initial pressurization of the system, the trigger (38) is squeezed, moving the cam (36) to the left and moving the threaded element (32) downwardly away from the threads on the rod. The handle (22) can then be moved in either direction, either to draw pressurization fluid into the system through the nozzle (26) or to provide initial pressurization of the angioplasty balloon as indicated by a pressure/vacuum manometer (28). The trigger is then released to engage the threaded component and the handle (22) is rotated to achieve final desired pressure in the angioplasty balloon as indicated in the manometer (28).

After the requisite period of time of pressurization, the trigger is activated and the piston (18) is free to move to the left, either by the pressure in the angioplasty liquid or by physically withdrawing the handle (22) to accomplish depressurization of the angioplasty balloon.

As can be seen best from FIG. 3, which is a partial sectional view of the barrel (10) and bearing member (30) taken along the line 3—3, the bearing member (30) is rigidly held in the barrel (10) by four bosses (31) on the outside of bearing member (30). These bosses (31) enter holes (35) in the barrel (10) and grip (14), this being possible due to expansion of the plastic barrel (10) and plastic pistol grip (14) by the bosses (31) when the bearing member (30) is pushed into the open (left) end of the barrel and grip.

For a more detailed understanding of the construction of the threaded half-nut and the trigger reference should be had to FIGS. 4A, 4B and 5. FIG. 4A shows a sectional view through a centerline of the components (32) in the form of a half-threaded nut (33), and FIG. 4B shows an end view thereof. The front and rear surfaces (50) (52) of the component form a tight fit with a slot in the bearing (30) to prevent forward or rear motion of the component (32). The T-shape slot (34) in the bottom of the component, is angled as shown to engage a corresponding T-shaped cam (36) carried by a web (90) on the trigger. The two side faces of the component (54) prevent lateral movement of the half-threaded nut when it is carried in the bearing (30).

Referring now to a more detailed view of the bearing, reference should be had to FIG. 6, which is an exploded view showing the bearing, the barrel (10) and the rear section (12) and the relationship of the various parts. The bearing (30) contains a bore (64) in which the rod (20) is positioned. This extended nature of the bearing prevents bending of the rod under the high pressure which can be generated in the angioplasty fluid. The rear surface (60) and front surface (62) in the bearing contact the corresponding surfaces (50) (52) of the half-threaded nut (32). The bosses (31) are shown in dotted lines in unassembled relation to the holes (35) shown in the right hand side of FIG. 6. As can be noted from the left hand portion of FIG. 6, the rear portion (12) contains a rear flange (70), a barrel section (72), and a bearing section (74) through which the rod (20) and its associated handle (22) extend. Internally coaxial fingers (76) are adapted to bear on the exterior of the end surface (66) of the bearing (30) to center and firmly position this bearing (30). When the rear cap (12) is in position and bonded or welded to the front portion (10-14) of the cylinder pistol grip assembly, this rear cap positively prevents rearward motion of the bearing, reinforcing the holding effect of the bosses (31) and the hole (35). The downwardly extending portion (78) completes the rear section of the pistol grip.

In FIG. 7, there is shown a isometric view of the assembled trigger and half-threaded nut for clarity of illustration.

In a preferred form of the invention, the rod (20) is preferably a glass filled nylon, as are the bearing (30) and the half-threaded nut (32). The trigger is preferably an acctal such as "Delrin TM" and the housing elements are polycarbonate, the front barrel preferably being a clear polycarbonate to permit observation of the filling of the piston. The rear can be clear or colored polycarbonate or ABS plastic. The principal requirement of the housing is that it be sufficiently rugged to withstand the internal pressure while also being sufficiently flexible to permit some expansion when the bosses (31) are shoved into the end of the barrel (10).

While one preferred embodiment of the invention has been described above, it is clear that numerous modifications thereof may be made without departing from the spirit of the invention.

I claim:

1. In a syringe assembly for accurate pressurization and rapid depressurization of a balloon catheter, the syringe assembly comprising:

a first threaded surface for advancement and retraction of a plunger within a barrel of the syringe assembly, said first threaded surface being on an elongated rod having a plunger in operative interengagement with the barrel;

a second threaded surface for engagement and disengagement with said first threaded surface to control speed of advancement and retraction of said plunger, said second threaded surface being on a component that is moveable in a direction generally transverse to the first threaded surface;

the improvement wherein;

a first cam surface is carried by said component and slanted at an angle to the axis of said barrel;

a second cam surface is carried by a trigger member moveable in a direction generally parallel to the barrel and slanted at an angle to the axis of said barrel;

said second cam surface positively engaging said first cam surface to move said component towards the first threaded surface when said trigger is moved in a first direction and to positively move said component away from said first threaded surface when said trigger is moved in a second direction, and a spring means for urging said trigger in said first direction.

2. The assembly of claim 1 wherein said trigger member is positioned in a pistol grip extending downwardly from said barrel.

3. The assembly of claim 2 wherein the spring means is mounted in said pistol grip.

4. The assembly of claim 2 wherein the rod is supported by a bearing member having transversely extending bosses which are held in holes formed in the barrel and pistol grip.

5. The assembly of claim 1 wherein said cam surface on said trigger is in the form of a T.

6. The assembly of claim 5 wherein said component has a T shaped slot engaging the T shaped cam on the trigger.

7. The assembly of claim 1 wherein said component is mounted in a bearing member for said rod, said bearing member being held against rearward movement by a rear portion of the assembly through which the rod extends.

8. The assembly of claim 1 wherein said trigger is mounted on ribs formed in the interior of a hollow handle extending downwardly from said barrel.

9. In a syringe assembly for accurate pressurization and rapid depressurization of a balloon catheter, the syringe assembly comprising:

a first threaded surface for advancement and retraction of a plunger within a barrel of the syringe assembly, said first threaded surface being on an elongated rod having a plunger in operative interengagement with the barrel;

a second threaded surface for engagement and disengagement with said first threaded surface to control speed of advancement and retraction of said plunger, said second threaded surface being on a component that is moveable in a direction generally transverse to the first threaded surface;

the improvement wherein;

a first cam surface is carried by a trigger member positioned in a pistol grip extending downwardly from said barrel, said trigger member being moveable in a direction generally parallel to the barrel;

said second cam surface positively engaging said first cam surface to move said component towards the first threaded surface when said trigger is moved in a first direction and to positively move said component away from said first threaded surface when said trigger is moved in a second direction, and a spring means mounted in said pistol grip for urging said trigger in said first direction.

10. The assembly of claim 9 wherein said cam surfaces are slanted at an angle to the axis of the barrel.

11. The assembly of claim 9 wherein the rod is supported by a bearing member having transversely extending bosses which are held in holes formed in the barrel and pistol grip.

12. The assembly of claim 10 wherein said cam surface on said trigger is in the form of a T.

13. The assembly of claim 12 wherein said component has a T shaped slot engaging the T shaped cam on the trigger.

14. The assembly of claim 9 wherein said component is mounted in a bearing member for said rod, said bearing member being held against rearward movement by a rear portion of the assembly through which the rod extends.

15. The assembly of claim 9 wherein said trigger is mounted on ribs formed in the interior of a hollow handle extending downwardly from said barrel.

16. In a syringe assembly for accurate pressurization and rapid depressurization of a balloon catheter, the syringe assembly comprising:

a first threaded surface for advancement and retraction of a plunger within a barrel of the syringe assembly, said first threaded surface being on an elongated rod having a plunger in operative interengagement with the barrel;

a second threaded surface for engagement and disengagement with said first threaded surface to control speed of advancement and retraction of said plunger, said second threaded surface being on a component that is moveable in a direction generally transverse to the first threaded surface;

the improvement wherein;

a cam surface is carried by said component;

a second cam surface is carried by a trigger member mounted on ribs formed in the interior of a hollow handle extending downwardly from said barrel, and moveable in a direction generally parallel to the barrel;

said second cam surface positively engaging said first cam surface to move said component towards the first threaded surface when said trigger is moved in a first direction and to positively move said component away from said first threaded surface when said trigger is moved in a second direction, and a spring means for urging said trigger in said first direction.

* * * * *

UNITED STATES PATENT AND TRADEMARK OFFICE
CERTIFICATE OF CORRECTION

PATENT NO. : 5,137,514

DATED : AUGUST 11, 1992

INVENTOR(S) : JAMES P. RYAN

It is certified that error appears in the above-identified patent and that said Letters Patent is hereby corrected as shown below:

Claim 9, Col. 5, line 13, after "by", insert --said component;--.

Claim 9, Col. 5, line 13, before "a", second occurance, insert --a second cam surface is carried by--.

Signed and Sealed this

Twenty-sixth Day of October, 1993

Attest:

BRUCE LEHMAN

Attesting Officer

Commissioner of Patents and Trademarks